United States Patent [19]

Spann

[11] Patent Number: 4,573,456
[45] Date of Patent: Mar. 4, 1986

[54] FOAM BODY SUPPORT

[75] Inventor: Donald C. Spann, Taylors, S.C.

[73] Assignee: Span-America Medical Systems, Inc., Greenville, S.C.

[21] Appl. No.: 738,501

[22] Filed: May 28, 1985

Related U.S. Application Data

[63] Continuation of Ser. No. 491,249, May 3, 1983, abandoned.

[51] Int. Cl.⁴ ............................................. A61F 13/00
[52] U.S. Cl. ................................ 128/80 R; 128/89 R
[58] Field of Search .................. 128/80 R, 80 A, 82, 128/83, 89 R, 68, 90, 87 R; 5/481, 431–448

[56] References Cited

U.S. PATENT DOCUMENTS

| | | | |
|---|---|---|---|
| Re. 30,444 | 12/1980 | Spann | 128/80 A |
| 2,371,788 | 3/1945 | Weeber | 5/481 |
| 2,763,013 | 9/1956 | Valkenburgh | 5/481 |
| 3,209,380 | 10/1965 | Watsky | 5/461 |
| 3,885,257 | 5/1975 | Rogers | 5/481 |

*Primary Examiner*—John D. Yasko
*Attorney, Agent, or Firm*—Dority & Manning

[57] ABSTRACT

A support is illustrated for the human body which is constructed essentially of a foam block having a plurality of spaced, aligned slits or narrow openings in the body support surface extending into the foam block with an enlarged air channel in the block into which the slit opens so that a discrete support is formed between adjacent slits and there respective channels.

1 Claim, 4 Drawing Figures

FOAM BODY SUPPORT

This application is a continuation of application Ser. No. 491,249, filed 05/03/83 now abandoned.

BACKGROUND OF THE INVENTION

The use of openings or narrow slots referred to herein as slits have been utilized wherever portions of the human body are to be supported by synthetic foam blocks in order to relieve the pressure upon the body and permit the dissipation of heat. Such openings or slits are illustrated in U.S. Pat. No Re. 30,444.

Such slits have been effective in relieving pressure points with the body between supporting entrance and exit surfaces of the to foam supports.

It is an important object of this invention to provide discrete support portions capable of supporting the human body between slits and the like in such a way as to improve the capabilities of the foam to dissipate heat and at the same time, provide uniform yielding supports for the body without excessive deformation.

An important purpose of this invention is to provide what is in effect a ring of air about a limb through the provision of radially spaced air passageways to eliminate heat and moisture from around the heat source which in this instance may be the lower leg of an orthopedic patient. A pumping action is provided by movement of the limb and the cool surrounding air acts to eliminate heat through convecion rather than by radiation. It is not necessary for the heat to travel through the foam. The supporting foam between the slits offers a firm support and avoids the bottoming out of the limb against the foam beneath the slits.

In the case of a hospitilized patient, the embodiment of the invention illustrated avoids pressure on acute angles such as the entry and exit points of the foam opposite the limb avoiding reddened hyperemia and ischemia palor which are conditions brought about by blockage of capillary blood flow as results from prolonged pressure across a portion of the body. The cock up body support is designed to carry away heat and body moisture as rapidly as possible through the slits and their respective air channels. The perspiration which the body produces causes masserated skin as a result of prolonged unrelieved contact with the body and this is another adverse effect sought to be eliminated through use of the invention.

It is an important object of this invention to provide maximum contact with the body by the foam in order to minimize pressure points while providing maximum air flow to carry away heat and moisture. This is accomplished by the support formed by the slots and air channels which provides maximum contact with the skin reducing concentrated pressure points while permitting the relief of heat and moisture.

The invention is illustrated in the drawings and preferred embodiments in the form of a cock up support such as illustrated in U.S. Pat. No. 3,903,878, the disclosure of which is incorporated herein by reference.

The invention contemplates use with a number of other foam block body supports and such may even be employed in a seat cushion, as illustrated in the drawing, or a back support, mattress, and the like.

SUMMARY OF THE INVENTION

It has been found that a body support may be constructed from a block of synthetic foam such as resilient, air permeable polyurethane such that a body supporting surface may be provided with spaced, aligned slits extending inwardly within the block and each opening into an enlarged air channel so that body heat and moisture may be dissipated from the air channels and a yieldable support offered by the discrete support member intermediate the slits. Thus, a support surface is formed by a number of segmented discrete support members formed by a number of spaced, aligned slits which open respectively into enlarged air channels which form in effect a layer or circle of air, the heat and moisture being conducted away through the slits and air passageways or channels while supporting a body portion without bottoming out and through offering support over a wide area while avoiding concentrated pressure points.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

The drawings illustrate a support for the human body constructed essentially of a synthetic foam block. A body supporting surface A of the synthetic foam block extends across a supported body portion of a human body. A plurality of spaced, aligned slits B open in the body supporting surfaces extending into the foam block. An enlarged air channel C in the foam block is aligned with each of the slits which open into a respective air channel. A segmented discrete support member D is formed between adjacent slits and their respective channels. Thus, body heat may be dissipated in the enlarged air channels and a yieldable support offered by the discrete support members.

Figure 1:
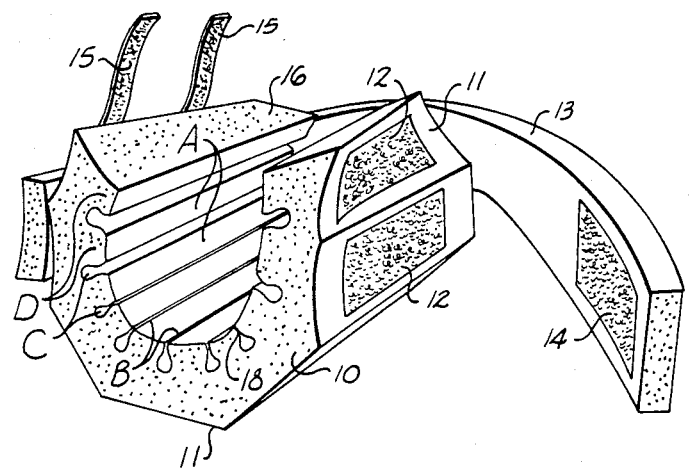
FIG. 1 is a perspective view of a cock up splint which is spread open to illustrate the various components including the slits and radially spaced air channels or passageways in the block of synthetic foam.
Figure 2:
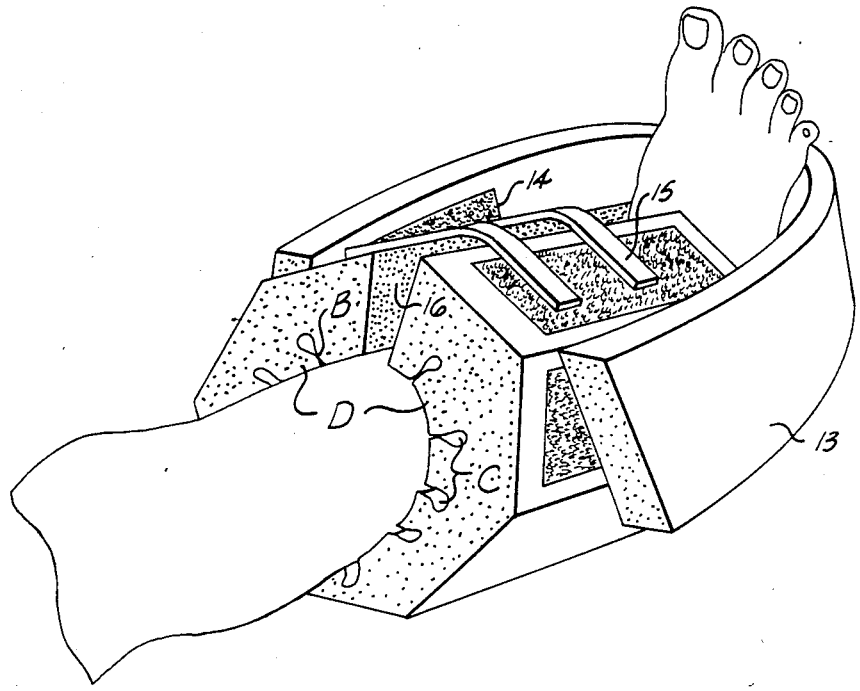
FIG. 2 is a perspective view similar to FIG. 1, but illustrating the support block as positioned about the limb of a user with the strap positioned to prevent foot drop.
Figure 3:
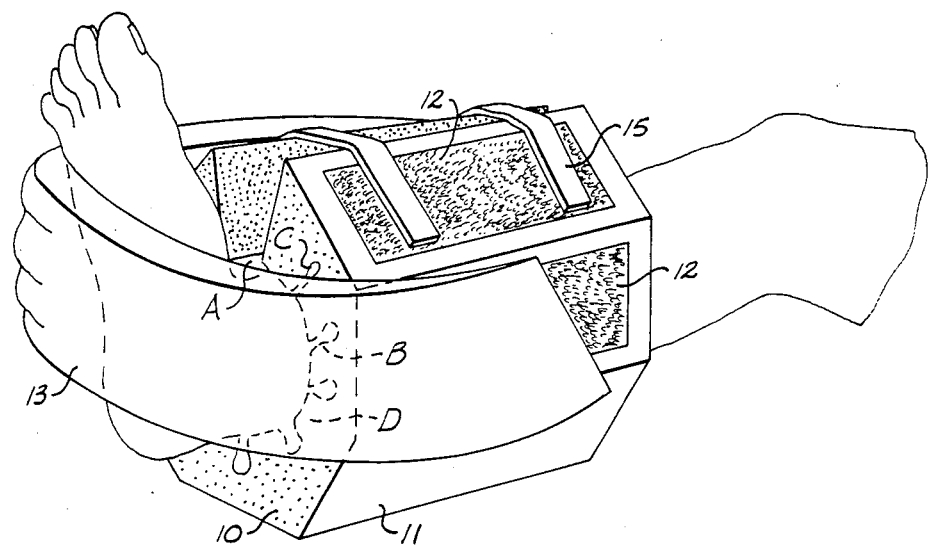
FIG. 3 is a perspective view looking toward the rear of FIG. 2.
Figure 4:
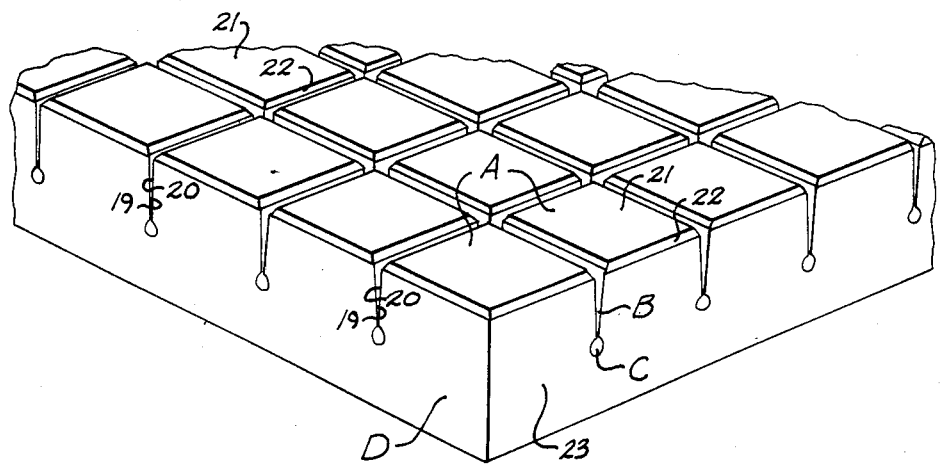
FIG. 4 is a perspective view illustrating a modified form of the invention utilized in connection with a foam seat member.

The drawings in FIGS. 1-3 a cock up support includes a foam block 10 having a number of angled, flat sides 11. A number of patches of Velcro 12 are secured on several faces 11 to accommodate a strap member 13. The strap has complementary sections of Velcro 14 on an inner surface thereof for attaching to the Velcro patches 12 for affixing strap in proper position as in FIGS. 2 and 3 for supporting the foot in upright position to avoid foot drop. Sections of strapping 15 which may be also constructed of Velcro may be passed across next adjacent strips 12 to close the opening 16 provided in the upper portion of the block. Such opening is provided to accommodate the limb of the user when placed therein and which may assume any width, but is best constructed to provide adjustment to a snug fit for the block about the limb of the user when the auxiliary straps 15 are fastened.

During construction the block is cut in a continuous motion of a wire saw which is like a bandsaw except that an abrasive wire is utilized. The bandsaw traverses a path generated by a template or otherwise controlled path in order to cut out the entire block with the faces and the slits and air channels of the invention in a single passage about the block. The block of the invention may be thus cut out of a larger foam block.

The slits B and the surface A are illustrated as being formed by a support passage of the wire saw in and out to form sides 18 which abut when no pressure is being applied to the foam block. The air channel is illustrated as being arcuate or perhaps tear-shaped and the slots open therein in such a way that the channel forms a terminus for the slots. The device may be designed to continue the slits on down below the air channel illustrated and a second ring of air channels may be provided (not shown). Alternatively, the slits may be formed in varying or alternating depths into the foam member.

In contrast to the abuting slit walls illustrated in FIGS. 1-3, FIG. 4 illustrates a seat formed of a rectangular flat block of synthetic foam wherein opposed walls 19 and 20 define the slits in the form of an open slot. In the seat illustrated two lines of slits cross at right angle to define rectangular upper surfaces 21 each of which is beveled as at 22. Thus, cubicle support members 23 are provided between the intersection rows of slits.

It is thus seen that a foam block has been utilized to provide maximum support with minimum pressure points and at the same time make provision for carrying away heat and moisture in a most effective manner.

While a preferred embodiment of the invention has been described using specific terms, such description is for illustrative purposes only and it is to be understood that changes and variations may be made without departing from the spirit or scope of the following claims.

What is claimed is:

1. A support for receiving a limb of an orthopedic patient constructed essentially of a synthetic foam block comprising:

an arcuate body supporting surface in said synthetic foam block extending across a supported body portion of a human body;

a plurality of spaced, aligned cuts having been formed in said foam block by sawing in a predetermined continuous motion opening in said arcuate body supporting surfaces extending into said foam block;

an enlarged air channel having been formed in said foam block by sawing in the same motion of the saw forming said cuts in said foam block aligned with and forming a terminus for each of said cuts;

a segmented discrete support member formed between adjacent cuts and their respective channels; and a foam strap with Velcro attachment means for receiving same to said block;

whereby body heat and moisture may be dissipated in air permeable enlarged air channels forming a ring of air about the limb and a yieldable support offered by said discrete support members.

* * * * *